United States Patent
Gleich et al.

(10) Patent No.: US 9,918,655 B2
(45) Date of Patent: Mar. 20, 2018

(54) APPARATUS AND METHOD FOR MEASURING THE INTERNAL PRESSURE OF AN EXAMINATION OBJECT

(75) Inventors: Bernhard Gleich, Hamburg (DE); Ingo Schmale, Hamburg (DE)

(73) Assignee: Koninklijke Philip N.V., Eindhoven (NL)

(*) Notice: Subject to any disclaimer, the term of this patent is extended or adjusted under 35 U.S.C. 154(b) by 1095 days.

(21) Appl. No.: 13/392,929

(22) PCT Filed: Aug. 17, 2010

(86) PCT No.: PCT/IB2010/053702
§ 371 (c)(1),
(2), (4) Date: Feb. 28, 2012

(87) PCT Pub. No.: WO2011/030249
PCT Pub. Date: Mar. 17, 2011

(65) Prior Publication Data
US 2012/0165649 A1   Jun. 28, 2012

(30) Foreign Application Priority Data
Sep. 14, 2009   (EP) .................................... 09170206

(51) Int. Cl.
*A61B 5/05* (2006.01)
*A61B 5/02* (2006.01)
*A61B 5/021* (2006.01)

(52) U.S. Cl.
CPC ................ *A61B 5/05* (2013.01); *A61B 5/021* (2013.01); *A61B 5/02007* (2013.01); *A61B 5/0515* (2013.01)

(58) Field of Classification Search
CPC ...... G01R 33/54; G01R 33/4818; G01B 7/02; G01B 7/16; G01B 7/28
(Continued)

(56) References Cited

U.S. PATENT DOCUMENTS 6,315,981 B1   11/2001   Unger
2003/0085703 A1   5/2003   Gleich
(Continued)

FOREIGN PATENT DOCUMENTS

DE   10151778   5/2003
EP   1304542   4/2003
(Continued)

OTHER PUBLICATIONS

Berkowitz, et al., "Hollow Metallic Microspheres Produced by Spark Erosion", Applied Physics Letters, AIP, American Institute of Physics, Melville, NY, US, vol. 85, No. 6, Jan. 1, 2004, pp. 940-942.
(Continued)

*Primary Examiner* — Joel F Brutus

(57) ABSTRACT

The present invention relates to an apparatus (100) for measuring the internal pressure of an examination object, in particular the internal pressure of a blood vessel, by use of a magnetic pressure measurement device (60, 70) introduced into the examination object, which apparatus comprises: —magnetic field generating means comprising magnetic field signal generator units (130) and magnetic field coils (136a, 136b, 136c) for generating a magnetic field for influencing the magnetization of the magnetic pressure measurement device (60, 70), receiving means comprising at least one signal receiving unit (140) and at least one receiving coil (148) for acquiring detection signals, which detection signals depend on the changes in magnetization of the magnetic pressure measurement device (60, 70) caused by the magnetic field and on the changes of the physical properties of the magnetic pressure measurement device caused by the internal pressure of the examination object, and evaluation means (153) for evaluating the detection signals of the magnetic pressure measurement device (60,
(Continued)

70) for determining the internal pressure of the examination object.

15 Claims, 10 Drawing Sheets

(58) Field of Classification Search
    USPC .......................................... 600/407, 409, 410
    See application file for complete search history.

(56) References Cited

U.S. PATENT DOCUMENTS

| 2003/0100830 | A1  | 5/2003  | Zhong et al. |         |
|--------------|-----|---------|--------------|---------|
| 2006/0030772 | A1* | 2/2006  | Hyde et al.  | 600/424 |
| 2006/0074479 | A1  | 4/2006  | Bailey       |         |
| 2006/0116590 | A1* | 6/2006  | Fayram et al.| 600/508 |
| 2006/0211938 | A1* | 9/2006  | Gleich et al.| 600/409 |
| 2007/0219611 | A1* | 9/2007  | Krever et al.| 623/1.11|
| 2007/0258888 | A1  | 11/2007 | Feldmann     |         |

FOREIGN PATENT DOCUMENTS

| JP | 2002511312   |    | 4/1999  |
|----|--------------|----|---------|
| JP | 2006503594   |    | 2/2006  |
| JP | 2007044262   | A  | 2/2007  |
| JP | 2009195614   | A  | 9/2009  |
| WO | WO9952505    |    | 10/1999 |
| WO | 2004091386   | A2 | 10/2004 |
| WO | 2004091390   | A2 | 10/2004 |
| WO | 2004091394   | A2 | 10/2004 |
| WO | 2004091395   | A2 | 10/2004 |
| WO | 2004091396   | A2 | 10/2004 |
| WO | 2004091397   | A2 | 10/2004 |
| WO | 2004091398   | A2 | 10/2004 |
| WO | 2004091408   |    | 10/2004 |
| WO | 2008078266   |    | 7/2008  |
| WO | WO2009074952 |    | 6/2009  |

OTHER PUBLICATIONS

Ren, et al., "Effects of Heat Treatment Temperature and Time on Structure and Static Magnetic Property of W-Type Ferrite Hollow Microspheres", Journal of Wuhan University of Technology-Mater. Sci. Ed., vol. 22, No. 1, Feb. 2007, pp. 168-170.

Zhang, et al., "Ferrite Hollow Spheres With Tunable Magnetic Properties", Think Solid Films, Elsevier-Sequoia S.A., Lausanne, Switzerland, vol. 515, No. 4, Dec. 5, 2006, pp. 2555-2561.

B. Gleich, et al., "Tomographic Imaging using the Nonlinear Response of Magnetic Particles", Nature, vol. 435, Jun. 30, 2005; doi: 10/1038, pp. 1214-1217.

\* cited by examiner

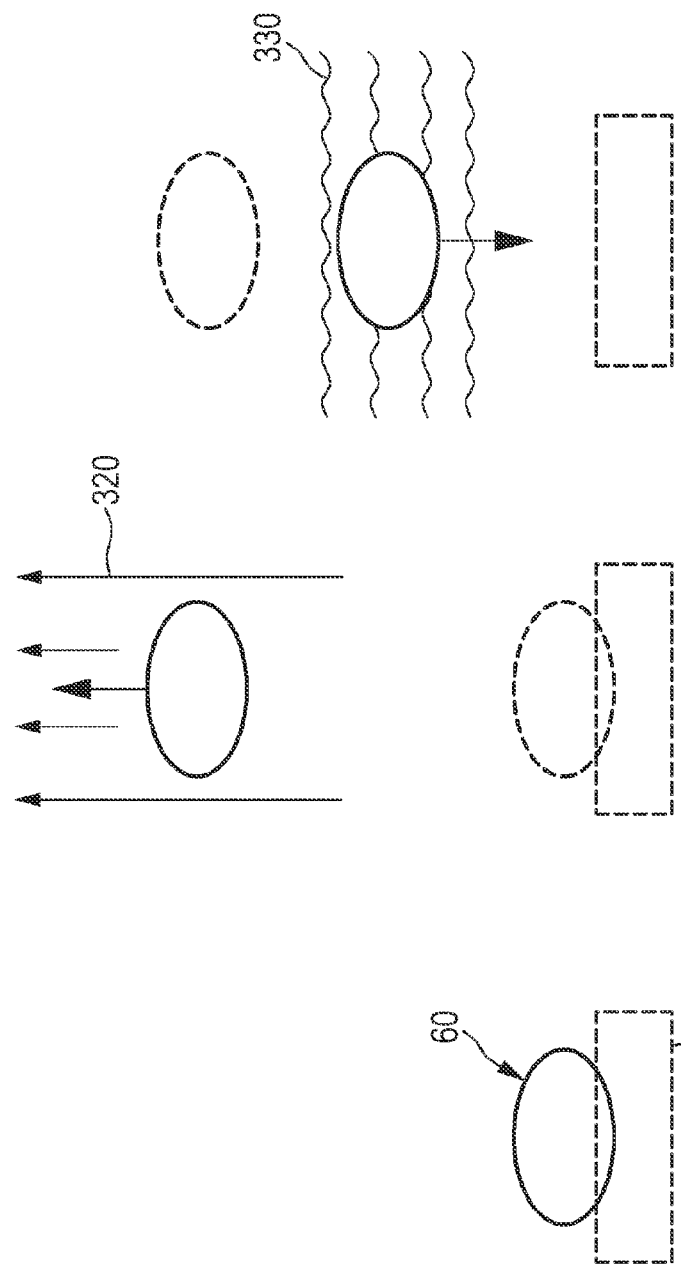

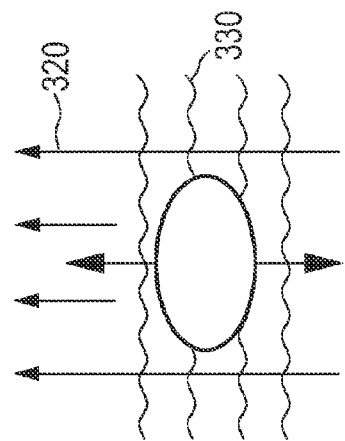
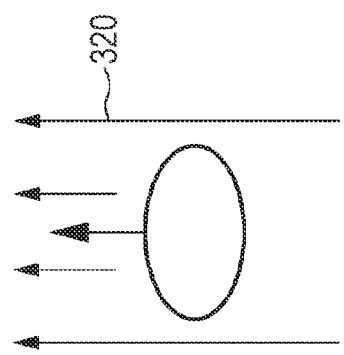
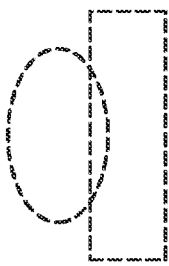
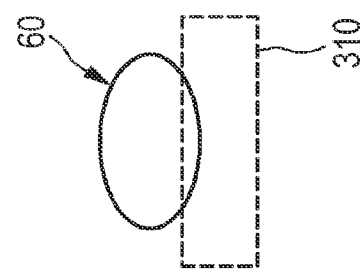
FIG. 9C
FIG. 9B
FIG. 9A

APPARATUS AND METHOD FOR MEASURING THE INTERNAL PRESSURE OF AN EXAMINATION OBJECT

FIELD OF THE INVENTION

The present invention relates to an apparatus and a method for measuring the internal pressure of an examination object, in particular the internal pressure of a blood vessel, by use of a magnetic pressure measurement device introduced into the examination object. Further, the present invention relates to such a magnetic pressure measurement device for the use in such an apparatus. Still further, the present invention relates to a computer program for implementing said method on a computer and for controlling such an apparatus.

BACKGROUND OF THE INVENTION

The internal pressure measurement of blood vessels, in particular the internal pressure measurement in lung arteries plays a decisive role in modern medicine. The pressure measurement of pulmonary arteries is an important quantity for lung and heart function assessment. This pressure measurement in pulmonary arteries is used for the diagnosis of shock states, primary pulmonary hypertension, pulmonary embolus or other severe left ventricular failure.

Unfortunately, the pulmonary artery pressure can only be measured reliably using an expensive catheter procedure. In medicine this procedure is usually referred to as pulmonary artery catheterization or referred to as Swan-Ganz catheter.

According to this procedure the catheter is introduced through a large vein, often the internal jugular, subclavian or femoral veins. From this entry side, it is threaded through the right atrium of the heart, the right ventricle and subsequently into the pulmonary artery. The standard pulmonary artery catheter has two lumens and is equipped with an inflatable balloon at its tip, which facilitates its placement into the pulmonary artery through the flow of blood. The balloon, when inflated, causes the catheter to "wedge" in a small pulmonary blood vessel. So wedged, the catheter can provide a measurement of the pressure in the left atrium of the heart.

Unfortunately, this procedure is due to its invasive complicated character not at all without risk, and complications can be live threatening. It can lead to arrhythmias, rupture of the pulmonary artery, thrombosis, infection, pneumothorax, bleeding, and other problems. Therefore many physicians minimize its use. Of course, other indirect methods like arterial gas levels and ultrasound are known to measure the pressure in the pulmonary arteries, but they just give a valuable insight into the disease, but no definitive answer. Reliable non-invasive methods have so far not been found.

Magnetic Particle Imaging (MPI) is an emerging medical imaging modality. The first versions of MPI were two-dimensional in that they produced two-dimensional images. Current and future versions will be three-dimensional (3D). A time-dependent, or 4D, image of a non-static object can be created by combining a temporal sequence of 3D images to a movie, provided the object does not significantly change during the data acquisition for a single 3D image.

MPI is a reconstructive imaging method, like Computed Tomography (CT) or Magnetic Resonance Imaging (MRI). Accordingly, an MP image of an object's volume of interest is generated in two steps. The first step, referred to as data acquisition, is performed using an MPI scanner. The MPI scanner has means to generate a static magnetic gradient field, called "selection field", which has a single field free point (FFP) at the isocenter of the scanner. In addition, the scanner has means to generate a time-dependent, spatially nearly homogeneous magnetic field. Actually, this field is obtained by superposing a rapidly changing field with a small amplitude, called "drive field", and a slowly varying field with a large amplitude, called "focus field". By adding the time-dependent drive and focus fields to the static selection field, the FFP may be moved along a predetermined FFP trajectory throughout a volume of scanning surrounding the isocenter. The scanner also has an arrangement of one or more, e.g. three, receive coils and can record any voltages induced in these coils. For the data acquisition, the object to be imaged is placed in the scanner such that the object's volume of interest is enclosed by the scanner's field of view, which is a subset of the volume of scanning.

The object must contain magnetic nanoparticles; if the object is an animal or a patient, a contrast agent containing such particles is administered to the animal or patient prior to and/or during the scan. During the data acquisition, the MPI scanner steers the FFP along a deliberately chosen trajectory that traces out the volume of scanning, or at least the field of view. The magnetic nanoparticles within the object experience a changing magnetic field and respond by changing their magnetization. The changing magnetization of the nanoparticles induces a time dependent voltage in each of the receive coils. This voltage is sampled in a receiver associated with the receive coil. The samples output by the receivers are recorded and constitute the acquired data. The parameters that control the details of the data acquisition make up the scan protocol.

In the second step of the image generation, referred to as image reconstruction, the image is computed, or reconstructed, from the data acquired in the first step. The image is a discrete 3D array of data that represents a sampled approximation to the position-dependent concentration of the magnetic nanoparticles in the field of view. The reconstruction is generally performed by a computer, which executes a suitable computer program. Computer and computer program realize a reconstruction algorithm. The reconstruction algorithm is based on a mathematical model of the data acquisition. As with all reconstructive imaging methods, this model is an integral operator that acts on the acquired data; the reconstruction algorithm tries to undo, to the extent possible, the action of the model.

Such an MPI apparatus and method have the advantage that they can be used to examine arbitrary examination objects—e.g. human bodies—in a non-destructive manner and without causing any damage and with a high spatial resolution, both close to the surface and remote from the surface of the examination object. Such an arrangement and method are generally known and are first described in DE 101 51 778 A1 and in Gleich, B. and Weizenecker, J. (2005), "Tomographic imaging using the nonlinear response of magnetic particles" in nature, vol. 435, pp. 1214-1217. The arrangement and method for magnetic particle imaging (MPI) described in that publication take advantage of the non-linear magnetization curve of small magnetic particles.

SUMMARY OF THE INVENTION

It is an object of the present invention to provide an improved apparatus and method for non-invasively measuring the internal pressure of an examination object, in particular the internal pressure of a blood vessel, which are, compared to methods known in the art, more accurate, easier to apply and which do not present a serious risk for the patient.

In a first aspect of the present invention an apparatus is presented which comprises:

magnetic field generating means comprising magnetic field signal generator units and magnetic field coils for generating a magnetic field for influencing the magnetization of the magnetic pressure measurement device, receiving means comprising at least one signal receiving unit and at least one receiving coil for acquiring detection signals, which detection signals depend on the changes in magnetization of the magnetic pressure measurement device caused by the magnetic field and on the changes of the physical properties of the magnetic pressure measurement device caused by the internal pressure of the examination object, and evaluation means for evaluating the detection signals of the magnetic pressure measurement device for determining the internal pressure of the examination object.

In a further aspect of the present invention, a corresponding method is presented.

In a further aspect of the present invention, a corresponding magnetic pressure measurement device for the use in the above-mentioned apparatus is presented, wherein said magnetic pressure measurement device is a deformable ferromagnetic body, in particular a hollow, substantially ellipsoidal or spherical-like body.

In still a further aspect of the present invention, a computer program is presented comprising program code means for causing a computer to control the apparatus according to the present invention to carry out the steps of the method according to the present invention when said computer program is carried out on the computer.

Preferred embodiments of the invention are defined in the dependent claims. It shall be understood that the claimed method, the claimed magnetic pressure measurement device and the claimed computer program have similar and/or identical preferred embodiments as the claimed apparatus and as defined in the dependent claims.

It has been recognized by the inventors that the major limitation of known pulmonary pressure measurement techniques, the complex, time-consuming and invasive surgery using a catheter, can be overcome by using the presented MPI technology. Hence, the inventors of the present invention have found a solution to use parts of a known MPI apparatus and method together with a magnetic pressure measurement device which has been introduced into the examination object of interest. Further, receiving means are added which are adapted to acquire detection signals which depend on the changes of the physical properties of said magnetic pressure measurement device caused by the internal pressure of the examination object. By providing evaluation means for evaluating the detection signals of the magnetic pressure measurement device the internal pressure of the examination object (the pulmonary arteries or other vessels) can be measured in a non-invasive way using MPI.

In other words, a magnetic field, generally a magnetic RF field, is applied to the internal pressure measurement device, which is positioned inside the examination object. At least one receiving coil is adapted for acquiring the detection signals which are influenced by the magnetic pressure measurement device.

The magnetic pressure measurement device can be imagined as a small ferromagnetic rod or disc which changes its physical properties due to pressure. If a pressure, e.g. the internal pulmonary artery pressure, is applied to the ferromagnetic rod, the rod changes its physical properties so that also the detection signals which are acquired by the receiving coil change. These changes of the detection signals particularly depend on the changes in magnetization of the magnetic pressure measurement device and on the changes of the physical properties of the magnetic pressure measurement device. Using the evaluation means the internal pressure of the examination object can be inferred from the evaluation of the change of the detection signals. In case the signal applied by the magnetic field generating means are sinusoidal signals the signal change can be evaluated by comparing the harmonics of the applied and the received signals.

The internal pressure can be observed as a function of time, which allows several ways of analysis. For example, the pressure is influenced by the heart action. Two typical and medically relevant pressure values are termed systolic (high pressure) and diastolic (low pressure). The described invention allows to determine pressure not only at these two special heart cycle moments, but at all moments in between, too, at a fine temporal resolution, from which additional medical understanding can be derived.

The internal pressure can be observed as a function of space, if several magnetic pressure measurement devices are employed. By these means, it can be examined if, e.g. the full systolic pressure arrives in all locations (e.g. limbs) of the body, or if there are mal-perfused areas. Additionally, by considering the temporal pressure evolution at all these points, it will be possible to determine the delay of the systolic wave reaching the locations for which the speed of the pressure wave can be determined. This gives a valuable insight in the quality of the arteries, in particular their stiffness as well as possibly occurring obstructions reducing pressure/speed/flow.

Furthermore, the internal pressure can be observed e.g. inside and outside an endovascular stent graft as used in the treatment of abdominal aortic aneurysm. Inside the graft, the pressure variation during the heart cycle will show maxima (systole) and minima (diastole). Outside the graft, which is inside the old aneurysm sac, the pressure variation is supposed to be much less, as long as there is no endoleak. An endo leak is a leak in the aneurysm sac after an endovascular repair. It is one of the common complications after such a repair. Therefore, regular control of the stent graft is required over a long period of time. So the described method allows a fast, non-invasive, and non-radiative follow-up assessment of the stent graft. It is furthermore preferred that the speed, with which the magnetic pressure measurement device moves through the examination object, is measured. This can, for example, be done by using the known MPI technique for localization of the examination object regularly at subsequent moments in time, wherefrom the speed of the object can be calculated. The speed measurement can be further improved by MPI imaging or continuous localization of the examination object.

In case the speed is measured, not only the static internal pressure of the examination object can be measured, but also the impact pressure, which is the sum of the static pressure (measured with the magnetic pressure measurement device) and the dynamic pressure (derived from the measured speed of the magnetic pressure measurement device and the density of the fluid in the examination object, e.g. the density of blood in case of a human patient).

However, depending on the application, the magnetic pressure measurement device is not always introduced into the examination object in a way that it moves through the examination object, as this is, for example, the case when using a bolus injection where the magnetic pressure measurement device freely moves with the blood flow within the examination object. In other applications the magnetic pressure measurement device can also be attached to a separate non-movable device or at a fixed position within the examination object. In this case the speed of the magnetic pressure measurement device (which is zero) is not of interest. However, in such an application it is possible to measure the pressure (e.g. the blood pressure) as well as the speed of the fluid (e.g. the speed of the blood flow) in the examination object at a certain fixed position over a longer period of time.

According to a preferred embodiment, the receiving means are adapted to acquire detection signals which depend on the changes of the shape of the magnetic pressure measurement device. If the magnetic pressure measurement device is made of a deformable material, the shape of the magnetic pressure measurement device changes due to the induced pressure in the examination object. This pressure-induced shape change can be mechanically modeled so that by comparing the signal answer with the applied signal the pressure can be calculated according to the mechanical model. For evaluating this pressure-induced shape change, the shape change of the magnetic pressure measurement device should be considerably high even for small pressure changes. The difference between the applied and the detected signals then result from a change in the magnetic anisotropy of the magnetic pressure measurement device.

According to a further preferred embodiment, it is therefore desirable that the evaluation means are adapted to evaluate the change of the magnetic anisotropy of the magnetic pressure measurement device caused by the change of the shape of the magnetic pressure measurement device. This means that, if the magnetic pressure measurement device has for example an ellipsoidal shape, the device becomes flatter whereby the magnetic anisotropy is increased. The change in anisotropy then results in a shift of the harmonics of the magnetic signal which is a reliable quantity for measuring the internal pressure of the examination object. More precisely, the shift of the harmonics of the magnetic signal is caused by the change of the magnetization curve (B-H curve) of the magnetic pressure measurement device which itself is caused by the shape change of the device.

In order to receive reliable measurement results it is therefore desirable that the magnetic pressure measurement device has an elongated shape since the demagnetization factor is smaller for elongated shapes so that the B-H curve is steeper and the magnetic pressure measurement device is saturated faster. In that case the magnetic pressure measurement device can be brought to the state of saturation even at a relatively small field strength of less than 3 mT.

Furthermore, it is important to consider that the applied magnetic field and the magnetic pressure measurement device have a constant and known angle to each other since the harmonics differ for different angles (i.e. are angular-dependent) for an anisotropic magnetic pressure measurement device. A first option to overcome this problem is by applying a static magnetic field so that the magnetic pressure measurement device is automatically aligned along the field lines in the direction of the smallest possible demagnetization factor.

Another option is to evaluate the detection signals along all spatial directions and then choosing the direction where the steepest B-H curve occurs. In this case a magnetic frequency field is applied by the magnetic field generating means and the detection signals, respectively the B-H curves are measured step by step for different spatial directions until the B-H curves have been measured for a plurality of spatial directions. In the next step the spatial direction where the steepest B-H curve occurs is selected and the corresponding detection signals are evaluated. Of course, it is also possible to interpolate the measured data in an appropriate way between different spatial directions in order to save measurement time and in order to being able to even more exactly determine the desired direction with the steepest B-H curve.

It has to be noted that both ways mentioned above for determining the direction with the steepest B-H curve can also be combined. For example by applying a static magnetic field so that the magnetic pressure measurement device is automatically aligned along the field lines in the direction of the smallest possible demagnetization factor and then still measuring the B-H curves for a plurality of spatial directions that are similar to the direction the magnetic pressure measurement device is aligned along. In this way the determination of the most adequate direction can be further improved.

According to a further preferred embodiment, the evaluation means are adapted to evaluate the change of the magnetic resonance of the magnetic pressure measurement device caused by the change of the shape of the magnetic pressure measurement device. In this embodiment, the applied magnetic field excites the magnetic pressure measurement device so that the device is forced to mechanically oscillate. The magnetic pressure measurement device therefore oscillates in such a way that its shape is compressed and released continuously over time due to the magnetic excitation. Due to the pressure-induced shape change (e.g. caused by the internal pressure of the pulmonary artery) a shift of the resonance frequencies of the oscillation of the magnetic pressure measurement device occurs. Similar to the above-mentioned embodiment, this shift of the resonance frequencies has an influence on the detection signals which are acquired by the receiving means. Therefore it is possible to determine the internal pressure of the examination object by evaluation the change of the detection signals using the evaluation means.

In order to improve the measurement quality it is furthermore preferred that the evaluation means are adapted to determine the internal pressure of the examination object by comparing the acquired detection signals with known reference signals. The comparison of the acquired detection signals with known reference signals is especially important due to the manufacturing tolerances of the magnetic pressure measurement device. In order to receive reliable reference signals detection signals of the magnetic pressure measurement device are evaluated in advance for different known temperatures and pressures. In this way the apparatus according to the present invention can be calibrated in advance and the influence of the pressure on the detection signals can be accurately determined according to these reference measurements.

According to a preferred embodiment of the present invention, the apparatus further comprises selection means comprising a selection field signal generator unit and selection field elements for generating a magnetic selection field having a pattern in space of its magnetic field strength such that a first sub-zone having a low magnetic field strength where the magnetization of the magnetic pressure measurement device is not saturated and a second sub-zone having a higher magnetic field strength where the magnetization of the magnetic pressure measurement device is saturated are formed in a field of view. Such selection means are known from the MPI principles of imaging magnetic particles within an examination object and are for instance described in the above-mentioned documents. The magnetic selection field is generally a magnetic gradient field. It has a substantially constant gradient in the direction of one axis (e.g. the horizontal axis) of the coil pair generating the selection field (the selection field elements) and reaches the value 0 (or almost 0) in the isocenter on this axis. Starting from this field-free point (FFP), the field strength of the magnetic selection field increases in all three spatial directions as the distance increases from the FFP. Since the magnetic field strength of the selection field is outside the FFP (in the second sub-zone) strong enough to keep the magnetic material of the magnetic pressure measurement device in the state of saturation, the magnetization of the magnetic pressure measurement device is not changed or influenced, respectively, by the magnetic field generating means when the device is located outside the FFP. This is according to the present invention especially advantageous if more than one magnetic pressure measurement device is used, since only the magnetic pressure measurement device which is located in or near the FFP contributes to the detection signals, whereas all other devices located outside the FFP do not contribute to the detection signals. The case, where many devices are used for the measurement, is very realistic since the device is not necessarily at the right time at the desired position (within the atrium, ventricle, artery) so that several devices may be needed for one pressure measurement assessment. In the case where more than one magnetic pressure measurement devices are attached to one or more separate non-movable devices, it is preferred to individually determine the pressure at the different locations of the several magnetic pressure measurement devices.

Furthermore, the magnetic selection field can be advantageous for blinding out other magnetic contaminations which harm the quality of the detection signals.

Another major advantage of the selection means is the possibility that the magnetic selection field coils can be used for the movement of the magnetic pressure measurement device through the examination object. For example, if the magnetic pressure measurement device is located in a pulmonary artery the FFP can be set to a point the device should not pass. The device is in this case always actively pulled away from the FFP so that the magnetic pressure measurement device cannot pass the FFP even if it is forced by the blood flow in the pulmonary artery. This is especially desirable if the internal pressure shall be measured in a specific region of the pulmonary arteries since the device then remains in this region and is not transported out of this region due to the blood flow.

According to a further embodiment of the present invention, it is preferred that the magnetic field generating means are furthermore adapted to change the position in space of the two sub-zones in the field of view by means of a magnetic drive field so that the magnetization of the magnetic pressure measurement device changes locally. This movement of the FFP respectively the two sub-zones is usually done by a magnetic drive field which is superposed to the selection field in the field of view. The FFP can therefore be moved along a predetermined trajectory which is either used for known MPI scanning or, which is especially advantageous according to the present invention, for moving the magnetic pressure measurement device along a predefined path. The drive field coils are able to generate sufficiently homogeneous fields in various directions at a sufficiently high speed and with a sufficiently large field strength that are required for the movement of the magnetic pressure measurement device. The use of these drive field coils therefore provides a high flexibility since they can be generated in any direction.

According to a further preferred embodiment of the present invention, the apparatus comprises focus means comprising a focus field signal generator unit and focus field coils for changing the position in space of the field of view by means of a magnetic focus field. Such a focus field has the same or a similar spatial distribution as the magnetic field for influencing the magnetization of the magnetic pressure measurement device. The focus field is basically used to move the position in space of the field of view. This is especially necessary since the field of view has a very limited size so that, if the magnetic pressure measurement device needs to be moved over a longer distance within the examination object (the patient), the focus field needs to change the position in space of the field of view in order to actively move and track the magnetic pressure measurement device along a predefined path.

Same or even better as the magnetic field coils for influencing the magnetization of the magnetic pressure measurement device, the magnetic focus field coils can be used for the movement of the magnetic pressure measurement device. These coils are able to generate sufficiently homogenous fields in various directions at a sufficiently high speed and with sufficiently large field strengths that are required for the movement of the magnetic pressure measurement device. The use of these focus field coils therefore provides a high flexibility since they can be generated in any direction.

According to a still further preferred embodiment of the present invention, the apparatus comprises control means for controlling said signal generator units to generate and provide control currents to the respective field coils to generate appropriate magnetic fields for moving the magnetic pressure measurement device through the examination object in a direction instructed by movement commands, and/or for holding the magnetic pressure measurement device at a constant position, in particular by use of a feedback mechanism based on real-time positioning. In contrast to the known pulmonary artery catheterization where a catheter is introduced into the pulmonary artery, the presented MPI apparatus allows to move the magnetic pressure measurement device through the examination object along any desired movement path without having to insert a catheter in a complicated surgical intervention. The planning procedure is thereby enormously facilitated and the accuracy of the placement of the magnetic pressure measurement device is significantly increased. Furthermore, the pressure measurement can be conducted much faster than using pulmonary artery catheterization since the control means are adapted to modify the magnetic fields very fast so that the magnetic pressure measurement device can be moved through the examination object and placed at the desired position in a very short time. Another major advantage of introducing control means for moving the magnetic pressure measurement device through the examination object is that, due to its non-invasive character, the measurement can be repeated many times without providing a risk for the patient.

Preferably, an interface for inputting such movement commands to the control unit is provided. Such an interface can be a user interface, such as a keyboard, pointer, computer mouse or joystick, or an interface for connection to another apparatus, such as a navigation unit or navigation tool on a computer, on which, for instance, the movement of the magnetic pressure measurement device has been planned, e.g. by use of image data of the patient obtained by use of another imaging modality, such as MR or CT. The control unit is then provided with movement commands and "translates" them into control signals for the respective signal generator units so that the appropriate magnetic fields will be generated.

Another advantage of introducing the control means for moving the magnetic pressure measurement device is that, compared to the known pulmonary artery catheterization, even in cases where the magnetic pressure measurement device is placed at a wrong position within the artery, the position can be easily corrected using the magnetic fields within the apparatus according to the present invention. Therefore, the application of the apparatus according to the present invention is, concerning security reasons, much more reliable and safe since the magnetic pressure measurement device can also not harm the tissue of the patient or be unintentionally placed at a critical position of the heart or the lung.

In practice, the device is usually injected intravenously prior to the application according to the present invention. After that it either flows driven by the blood flow or is actively moved through the right-heart chambers and from there to the pulmonary arteries. In the lung capillaries, the device usually gets stuck. If the device is then stuck it loses its function since the device cannot be compressed, respectively expanded, in response to the pressure of the pulmonary artery. If detection signals would be acquired in this situation the pressure measurement would fail and a correct pressure of the pulmonary artery could not be determined. Therefore, it is a major advantage that, according to the above-mentioned embodiment, the control means are adapted to generate and provide control currents to the respective field coils to generate appropriate magnetic fields for moving the magnetic pressure measurement device and/or for holding the device at a constant position. By this technique the device can be pulled away from its stuck position within the lung capillaries so that the shape of the device can be freely influenced again by the lung pressure. The detection signals can then either be acquired while the device freely moves through the lung together with the blood flow, or an appropriate magnetic field can be generated for holding the magnetic pressure measurement device at a constant position, where the device can freely move.

According to a still further preferred embodiment of the present invention, the apparatus comprises processing means for processing the detection signals acquired when appropriate magnetic fields are applied for localizing the magnetic pressure measurement device within the examination object and for determining the position in space of the magnetic pressure measurement device within the examination object from the processed detection signals. These processing means are especially desirable if the localization and the visualization of the magnetic pressure measurement device is of special interest. Within the MPI technique the device can then be visualized during the movement through the examination object (during the movement through the arteries or the veins). It is especially advantageous that the device can thereby be moved and localized alternately or even almost simultaneously without additional equipment, such as additional hardware for localization, e.g. a camera system or an x-ray system. This means, that the control until then generates control commands for the signal generator units to generate and provide control currents to the respective field coils to generate appropriate magnetic fields for imaging the device.

This is especially advantageous since it enables the apparatus according to the present invention to easily check the correct movement and position of the device during its movement through the examination object without the use of another imaging modality, such as x-ray or CT. Since no x-ray or CT is needed it also reduces the dosage for the patient and furthermore no additional hardware is required for this imaging functionality.

Since the signals can be very accurately detected and acquired by the receiving means, the magnetic pressure measurement device can be reliably positioned and the defined position can easily be checked and corrected if necessary.

According to a still further preferred embodiment of the present invention the magnetic pressure measurement device is attached to or integrated whithin a fixation device, in particular a stent, a stent graft or a Guglielmi detachable coil, wherein the fixation device is placed at a fixed position whithin the examination object. This embodiment is especially advantageous for assessing phenomena, such as restenosis, abdominal aortic aneurysm (AAA) or endoleakage in a non-invasive low-cost way.

Restenosis can be defined as a reduction in the circumference of the lumen of 50% or more. Restenosis often occurs after stent placement, not only in the case of bare-metal stents but also with drug-eluting stents. A stent is an artificial tube inserted into a natural passage/conduit in the body to prevent or counteract a disease-induced localized flow constriction. Assessing the severity of a restenosis has so far been done via lumen imaging, in particular using CT- or MR-imaging techniques. In most cases a catheter has so far been inserted into the vessel to measure the pressure drop across the stent. However, such techniques were used during percutaneous translumincal coronary angioplasty (PTCA), when a catheter is already in the body. Comparing pressure in front of and after the stent placement procedure allowed assessing the success of the operation. However, no simple low-cost solution has so far existed to assess restenosis via a routine control as a follow up of the operation.

The other phenomena which can be accessed with the new technique presented herein is abdominal aortic aneurysm (AAA). AAA is a ballooning of the abdominal aorta, a condition that affects 3 million people worldwide. Due to a progressive weakening of the vessel wall, AAAs gradually balloon, and if left untreated, the enlargement can lead to aortic rupture—fatal in nearly 80% of cases. If the diameter of the aneurysm exceeds 5.0 cm, surgical intervention is indicated, which has primarily been in the form of open abdominal surgery. In recent years a less-invasive procedure of inserting an endovascular stent graft has become more prevalent. Despite such advances, between 40-50% of patients who undergo the procedure develop a serious complication in which the aneurysmal sac is not completely isolated, leading to recurrent pressurization of the sac (endotension) and/or endoleaks. Therefore, post-operative monitoring has so far been crucial, and as a result the FDA required frequent monitoring (currently done by CT angiography scans) for patients who have undergone the procedure. Currently, all patients with endovascular aneurysm repair must undergo lifelong periodic imaging to evaluate the stent graft.

With the presented apparatus for measuring the internal pressure of an examination object it is now possible to address the above-mentioned medical problems in a non-invasive manner. According to the embodiment mentioned above the magnetic pressure measurement device is attached to or integrated whithin a fixation device, wherein the fixation device is placed at a fixed position whithin the examination object. A possible application is the attachment of the magnetic pressure measurement device to stents or stent grafts which are inserted into an artery of the patient. It is to be understood that in several applications it is also useful to attach more than one magnetic pressure measurement device to the used fixation device. In case of a stent or stent graft it would, for example, be possible to attach several magnetic pressure measurement devices at each side and in the middle part of the stent or stent graft. This enables measuring the pressure in front of, in, behind, as well as outside of the stent or stent graft in the above described way by making use of the MPI technique. It is also possible to integrate the magnetic pressure measurement devices into a Gugliemi detachable doil.

In contrast to the invasive techniques mentioned above this enables to non-invasively monitor the pressure, e.g within an aneurysm sac. Furthermore, this approach is less cost intensive and more comfortable for the patient.

As already mentioned above, concerning the magnetic pressure measurement device itself, it is especially preferred that it is made of a deformable ferromagnetic body, in particular a hollow, substantially ellipsoidal or spherical-like body. The magnetic pressure measurement device can for example be made of an iron mantel which is in its inner core either evacuated or filled with a gas, wherein the gas is preferably close to the condensation point under measurement conditions.

By this gas filling the magnetic pressure measurement device is especially deformable so that very small pressure variations can be detected. Concerning the size of the device a size of about 50 µm (or, more general, between 10 and 100 µm) is especially desirable in an exemplary embodiment. It has to be noted that an ellipsoidal or spherical-like shape of the magnetic pressure measurement device is advantageous but not required. The magnetic pressure measurement device can also be made of two half-shells which are attached to each other via a small plate in between those to half-shells.

As already mentioned above, it is, according to an embodiment of the present invention, especially desirable that said device is magnetically unisotropic. These unisotropic characteristics are desirably realized by an elongated shape of the device so that the demagnetization factor is kept as small as possible and the B-H curve is as steep as possible.

According to an embodiment of the present invention, the magnetic pressure measurement device further comprises a protective casing so that the magnetic pressure measurement device is free to change its shape within this protective casing. If the device is, as already mentioned above, stuck in the lung capillaries it still does not lose its function if it is equipped with such a protective casing. Even though the whole element (the device including the protective casing) is then stuck, the magnetic pressure measurement device is still free to change its shape within such a protective casing so that correct detection signals can still be acquired during the measurement even if the device is stuck. In this embodiment therefore a special technique as the one mentioned above for pulling the device out of its stuck position using appropriate magnetic fields is not necessary anymore.

BRIEF DESCRIPTION OF THE DRAWINGS

These and other aspects of the invention will be apparent from and elucidated with reference to the embodiment(s) described hereinafter. In the following drawings
FIGS. 8A-8C show a first embodiment of the measurement procedure in a schematic and simplified manner,
FIGS. 9A-9C show a second embodiment of the measurement procedure in a schematic and simplified manner.

DETAILED DESCRIPTION OF THE INVENTION

Before the details of the present invention shall be explained, basics of magnetic particle imaging shall be explained in detail with reference to FIGS. 1 to 4. In particular, two embodiments of an MPI scanner for medical diagnostics will be described. An informal description of the data acquisition is also given. The similarities and differences between the two embodiments will be pointed out.

Figure 1:
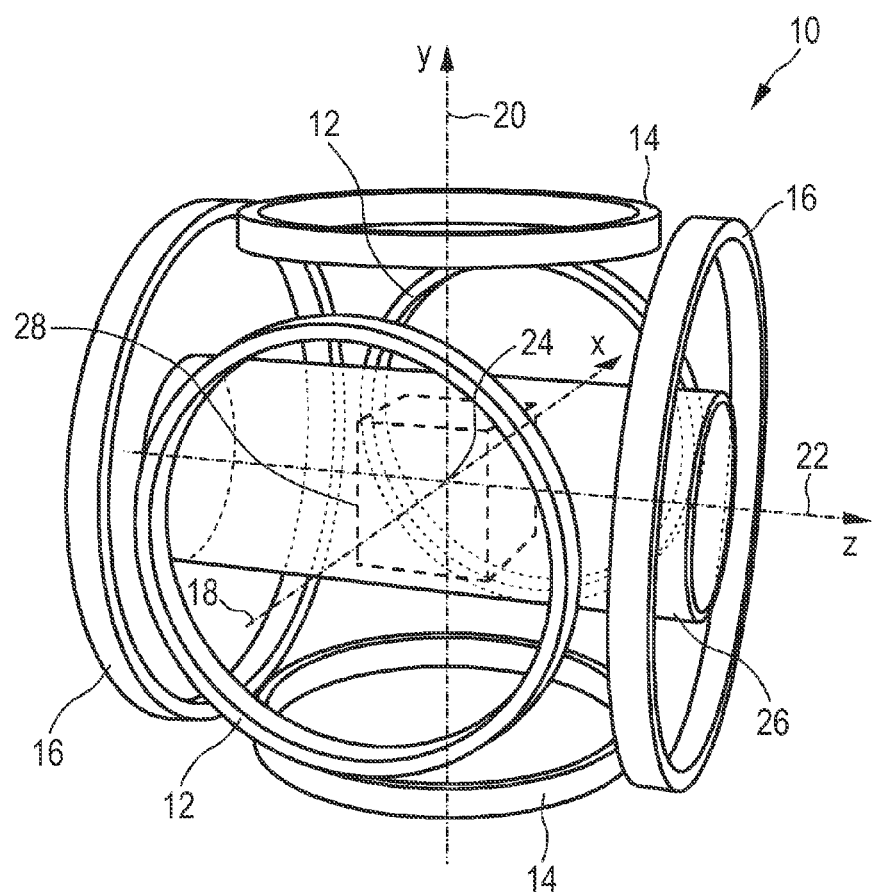
FIG. 1 shows a first embodiment of an MPI apparatus.

The first embodiment 10 of an MPI scanner shown in FIG. 1 has three prominent pairs 12, 14, 16 of coaxial parallel circular coils, each pair being arranged as illustrated in FIG. 1. These coil pairs 12, 14, 16 serve to generate the selection field as well as the drive and focus fields. The axes 18, 20, 22 of the three coil pairs 12, 14, 16 are mutually orthogonal and meet in a single point, designated the isocenter 24 of the MPI scanner 10. In addition, these axes 18, 20, 22 serve as the axes of a 3D Cartesian x-y-z coordinate system attached to the isocenter 24. The vertical axis 20 is nominated the y-axis, so that the x and z-axes are horizontal. The coil pairs 12, 14, 16 are also named after their axes. For example, the y-coil pair 14 is formed by the coils at the top and the bottom of the scanner. Moreover, the coil with the positive (negative) y-coordinate is called the $y^+$-coil ($y^-$-coil), and similarly for the remaining coils. When more convenient, the coordinate axes and the coils shall be labelled with $x_1$, $x_2$, and $x_3$, rather than with x, y, and z.

The scanner 10 can be set to direct a predetermined, time dependent electric current through each of these coils 12, 14, 16, and in either direction. If the current flows clockwise around a coil when seen along this coil's axis, it will be taken as positive, otherwise as negative. To generate the static selection field, a constant positive current $I^S$ is made to flow through the $z^+$-coil, and the current $-I^S$ is made to flow through the $z^-$-coil. The z-coil pair 16 then acts as an anti-parallel circular coil pair.

It should be noted here that the arrangement of the axes and the nomenclature given to the axes in this embodiment is just an example and might also be different in other embodiments. For instance, in practical embodiments the vertical axis is often considered as the z-axis rather than the y-axis as in the present embodiment. This, however, does not generally change the function and operation of the device and the effect of the present invention.

Figure 2:
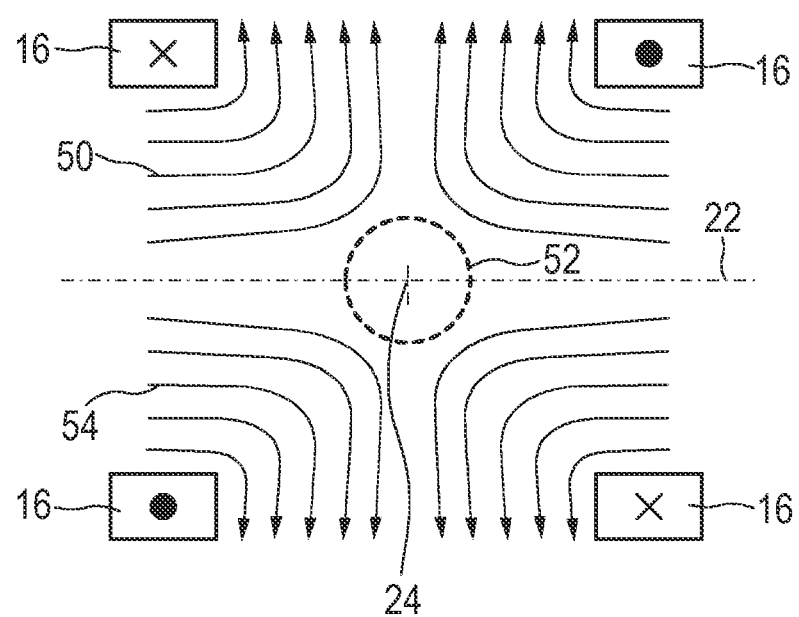
FIG. 2 shows an example of the selection field pattern produced by an apparatus as shown in FIG. 1.

The magnetic selection field which is generally a gradient magnetic field is represented in FIG. 2 by the field lines 50. It has a substantially constant gradient in the direction of the (e.g. horizontal) z-axis 22 of the z-coil pair 16 generating the selection field and reaches the value zero in the isocenter 24 on this axis 22. Starting from this field-free point (not individually shown in FIG. 2), the field strength of the magnetic selection field 50 increases in all three spatial directions as the distance increases from the field-free point. In a first sub-zone or region 52 which is denoted by a dashed line around the isocenter 24 the field strength is so small that the magnetization of particles present in that first sub-zone 52 is not saturated, whereas the magnetization of particles present in a second sub-zone 54 (outside the region 52) is in a state of saturation. The field-free point or first sub-zone 52 of the scanner's field of view 28 is preferably a spatially coherent area; it may also be a punctiform area, a line or a flat area. In the second sub-zone 54 (i.e. in the residual part of the scanner's field of view 28 outside of the first sub-zone 52) the magnetic field strength of the selection field is sufficiently strong to keep the magnetic particles in a state of saturation.

By changing the position of the two sub-zones 52, 54 within the field of view 28, the (overall) magnetization in the field of view 28 changes. By measuring the magnetization in the field of view 28 or physical parameters influenced by the magnetization, information about the spatial distribution of the magnetic particles in the field of view 28 can be obtained. In order to change the relative spatial position of the two sub-zones 52, 54 in the field of view 28, further magnetic fields, i.e. the magnetic drive field, and, if applicable, the magnetic focus field, are superposed to the selection field 50 in the field of view 28 or at least in a part of the field of view 28.

To generate the drive field, a time dependent current $I^D_1$ is made to flow through both x-coils 12, a time dependent current $I^D_2$ through both y-coils 14, and a time dependent current $I^D_3$ through both z-coils 16. Thus, each of the three coil pairs acts as a parallel circular coil pair. Similarly, to generate the focus field, a time dependent current $I^F_1$ is made to flow through both x-coils 12, a current $I^F_2$ through both y-coils 14, and a current $I^F_3$ through both z-coils 16.

It should be noted that the z-coil pair 16 is special: It generates not only its share of the drive and focus fields, but also the selection field. The current flowing through the $z^+$-coil is $I^D_3 + I^F_3 + I^S$. The current flowing through the remaining two coil pairs 12, 14 is $I^D_k + I^F_k$, k=1, 2. Because of their geometry and symmetry, the three coil pairs 12, 14, 16 are well decoupled. This is wanted.

Being generated by an anti-parallel circular coil pair, the selection field is rotationally symmetric about the z-axis, and its z-component is nearly linear in z and independent of x and y in a sizeable volume around the isocenter 24. In particular, the selection field has a single field free point (FFP) at the isocenter. In contrast, the contributions to the drive and focus fields, which are generated by parallel circular coil pairs, are spatially nearly homogeneous in a sizeable volume around the isocenter 24 and parallel to the axis of the respective coil pair. The drive and focus fields jointly generated by all three parallel circular coil pairs are spatially nearly homogeneous and can be given any direction and strength, up to some maximum strength. The drive and focus fields are also time dependent. The difference between the focus field and the drive field is that the focus field varies slowly in time and has a large amplitude while the drive field varies rapidly and has a small amplitude. There are physical and biomedical reasons to treat these fields differently. A rapidly varying field with a large amplitude would be difficult to generate and hazardous to the patient.

In a practical embodiment the FFP can be considered as a mathematical point, at which the magnetic field is assumed to be zero. The magnetic field strength increases with increasing distance from the FFP, wherein the increase rate might be different for different directions (depending e.g. on the particular layout of the device). As long as the magnetic field strength is below the field strength required for bringing a magnetic particles into the state of saturation, the particle actively contributes to the signal generation of the signal measured by the device; otherwise, the particles is saturated and does not generate any signal.

The embodiment 10 of the MPI scanner has at least one further pair, preferably three further pairs, of parallel circular coils, again oriented along the x-, y-, and z-axes. These coil pairs, which are not shown in FIG. 1, serve as receive coils. As with the coil pairs 12, 14, 16 for the drive and focus fields, the magnetic field generated by a constant current flowing through one of these receive coil pairs is spatially nearly homogeneous within the field of view and parallel to the axis of the respective coil pair. The receive coils are supposed to be well decoupled. The time dependent voltage induced in a receive coil is amplified and sampled by a receiver attached to this coil. More precisely, to cope with the enormous dynamic range of this signal, the receiver samples the difference between the received signal and a reference signal. The transfer function of the receiver is non-zero from DC up to the point where the expected signal level drops below the noise level.

The embodiment 10 of the MPI scanner shown in FIG. 1 has a cylindrical bore 26 along the z-axis 22, i.e. along the axis of the selection field. All coils are placed outside this bore 26. For the data acquisition, the patient (or examination object) to be imaged (or treated) is placed in the bore 26 such that the patient's volume of interest—that volume of the patient (or examination object) that shall be imaged (or treated)—is enclosed by the scanner's field of view 28—that volume of the scanner whose contents the scanner can image. The patient (or examination object) is, for instance, placed on a patient table. The field of view 28 is a geometrically simple, isocentric volume in the interior of the bore 26, such as a cube, a ball, or a cylinder. A cubical field of view 28 is illustrated in FIG. 1.

The size of the first sub-zone 52 is dependent on the one hand on the strength of the gradient of the magnetic selection field and on the other hand on the field strength of the magnetic field required for saturation. For a sufficient saturation of the magnetic particles at a magnetic field strength of 80 A/m and a gradient (in a given space direction) of the field strength of the magnetic selection field amounting to $50 \times 10^3$ A/m², the first sub-zone 52 in which the magnetization of the particles is not saturated has dimensions of about 1 mm (in the given space direction).

The patient's volume of interest is supposed to contain magnetic nanoparticles. Especially prior to a therapeutic and/or diagnostic treatment of, for example, a tumor, the magnetic particles are positioned in the volume of interest, e.g. by means of a liquid comprising the magnetic particles which is injected into the body of the patient (examination object) or otherwise administered, e.g. orally, to the patient.

An embodiment of magnetic particles comprises, for example, a spherical substrate, for example, of glass which is provided with a soft-magnetic layer which has a thickness of, for example, 5 nm and consists, for example, of an iron-nickel alloy (for example, Permalloy). This layer may be covered, for example, by means of a coating layer which protects the particle against chemically and/or physically aggressive environments, e.g. acids. The magnetic field strength of the magnetic selection field 50 required for the saturation of the magnetization of such particles is dependent on various parameters, e.g. the diameter of the particles, the used magnetic material for the magnetic layer and other parameters.

In the case of e.g. a diameter of 10 μm, a magnetic field of approximately 800 A/m (corresponding approximately to a flux density of 1 mT) is then required, whereas in the case of a diameter of 100 μm a magnetic field of 80 A/m suffices. Even smaller values are obtained when a coating of a material having a lower saturation magnetization is chosen or when the thickness of the layer is reduced. Magnetic particles that can generally be used are available on the market under the trade name Resovist.

In practice, magnetic particles commercially available under the trade name Resovist (or similar magnetic particles) are often used, which have a core of magnetic material or are formed as a massive sphere and which have a diameter in the range of nanometers, e.g. 40 or 60 nm.

For further details of the generally usable magnetic particles and particle compositions, the corresponding parts of EP 1304542, WO 2004/091386, WO 2004/091390, WO 2004/091394, WO 2004/091395, WO 2004/091396, WO 2004/091397, WO 2004/091398, WO 2004/091408 are herewith referred to, which are herein incorporated by reference. In these documents more details of the MPI method in general can be found as well.

The data acquisition starts at time $t_s$ and ends at time $t_e$. During the data acquisition, the x-, y-, and z-coil pairs 12, 14, 16 generate a position- and time dependent magnetic field, the applied field. This is achieved by directing suitable currents through the coils. In effect, the drive and focus fields push the selection field around such that the FFP moves along a preselected FFP trajectory that traces out the volume of scanning—a superset of the field of view. The applied field orientates the magnetic nanoparticles in the patient. As the applied field changes, the resulting magnetization changes too, though it responds nonlinearly to the applied field. The sum of the changing applied field and the changing magnetization induces a time dependent voltage $V_k$ across the terminals of receive coil pair along the $x_k$-axis. The associated receiver converts this voltage to a signal $S_k(t)$, which it samples and outputs.

It is advantageous to receive or to detect signals from the magnetic particles located in the first sub-zone 52 in another frequency band (shifted to higher frequencies) than the frequency band of the magnetic drive field variations. This is possible because frequency components of higher harmonics of the magnetic drive field frequency occur due to a change in magnetization of the magnetic particles in the scanner's field of view 28 as a result of the non-linearity of the magnetization characteristics.

Figure 3:
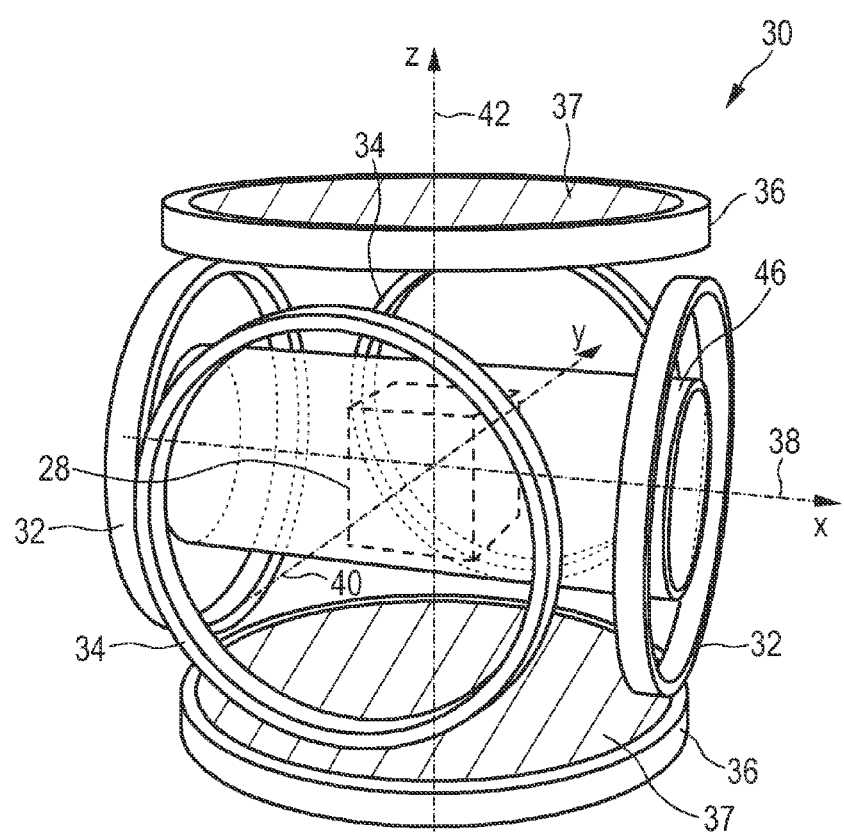
FIG. 3 shows a second embodiment of an MPI apparatus.

Like the first embodiment 10 shown in FIG. 1, the second embodiment 30 of the MPI scanner shown in FIG. 3 has three circular and mutually orthogonal coil pairs 32, 34, 36, but these coil pairs 32, 34, 36 generate the selection field and the focus field only. The z-coils 36, which again generate the selection field, are filled with ferromagnetic material 37. The z-axis 42 of this embodiment 30 is oriented vertically, while the x- and y-axes 38, 40 are oriented horizontally. The bore 46 of the scanner is parallel to the x-axis 38 and, thus, perpendicular to the axis 42 of the selection field. The drive field is generated by a solenoid (not shown) along the x-axis 38 and by pairs of saddle coils (not shown) along the two remaining axes 40, 42. These coils are wound around a tube which forms the bore. The drive field coils also serve as receive coils. The signals picked up by the receive coils are sent through a high-pass filter that suppresses the contribution caused by the applied field.

To give a few typical parameters of such an embodiment: The z-gradient of the selection field, G, has a strength of $G/\mu_0=2.5$ T/m, where $\mu_0$ is the vacuum permeability. The selection field generated does either not vary at all over the time or the variation is comparably slow, preferably between approximately 1 Hz and approximately 100 Hz. The temporal frequency spectrum of the drive field is concentrated in a narrow band around 25 kHz (up to approximately 150 kHz). The useful frequency spectrum of the received signals lies between 50 kHz and 1 MHz (eventually up to approximately 15 MHz). The bore has a diameter of 120 mm. The biggest cube 28 that fits into the bore 46 has an edge length of 120 mm/$\sqrt{2}\approx$vmm.

As shown in the above embodiments the various magnetic fields can be generated by coils of the same coils pairs and by providing these coils with appropriately generated currents. However, and especially for the purpose of a signal interpretation with a higher signal to noise ratio, it may be advantageous when the temporally constant (or quasi constant) selection field and the temporally variable drive field and focus field are generated by separate coil pairs. Generally, coil pairs of the Helmholtz type can be used for these coils, which are generally known, e.g. from the field of magnetic resonance apparatus with open magnets (open MRI) in which a radio frequency (RF) coil pair is situated above and below the region of interest, said RF coil pair being capable of generating a temporally variable magnetic field. Therefore, the construction of such coils need not be further elaborated herein.

In an alternative embodiment for the generation of the selection field, permanent magnets (not shown) can be used. In the space between two poles of such (opposing) permanent magnets (not shown) there is formed a magnetic field which is similar to that shown in FIG. 2, that is, when the opposing poles have the same polarity. In another alternative embodiment, the selection field can be generated by a mixture of at least one permanent magnet and at least one coil.

Figure 4:
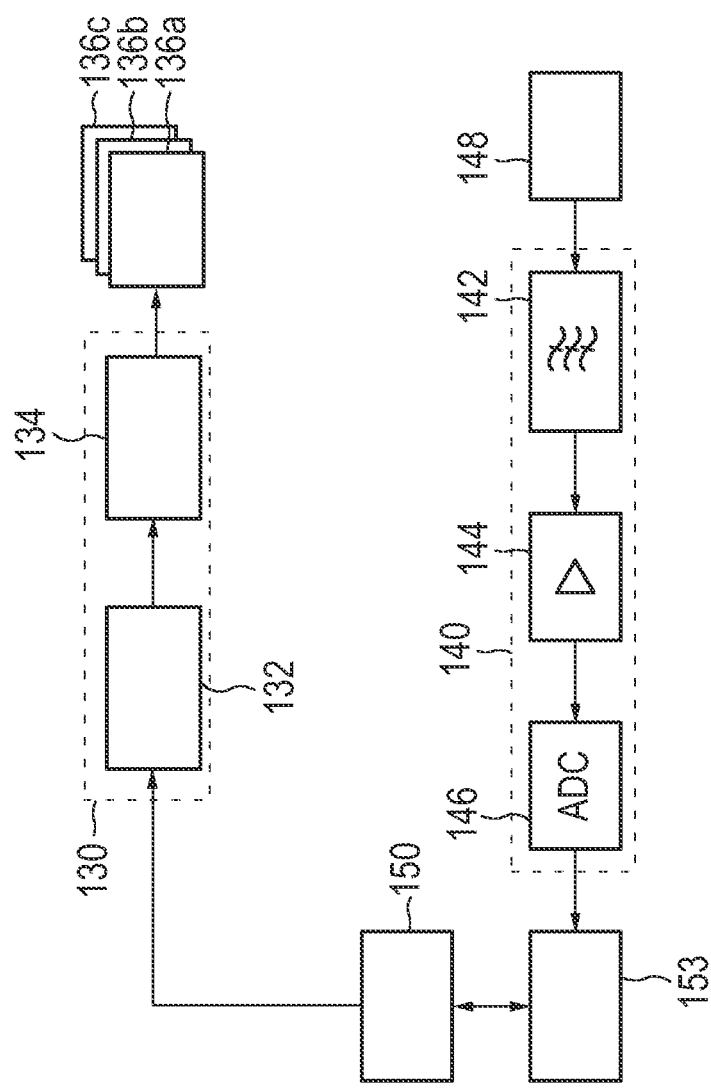
FIG. 4 shows a block diagram of a first embodiment of the MPI apparatus according to the present invention.
Figure 5:
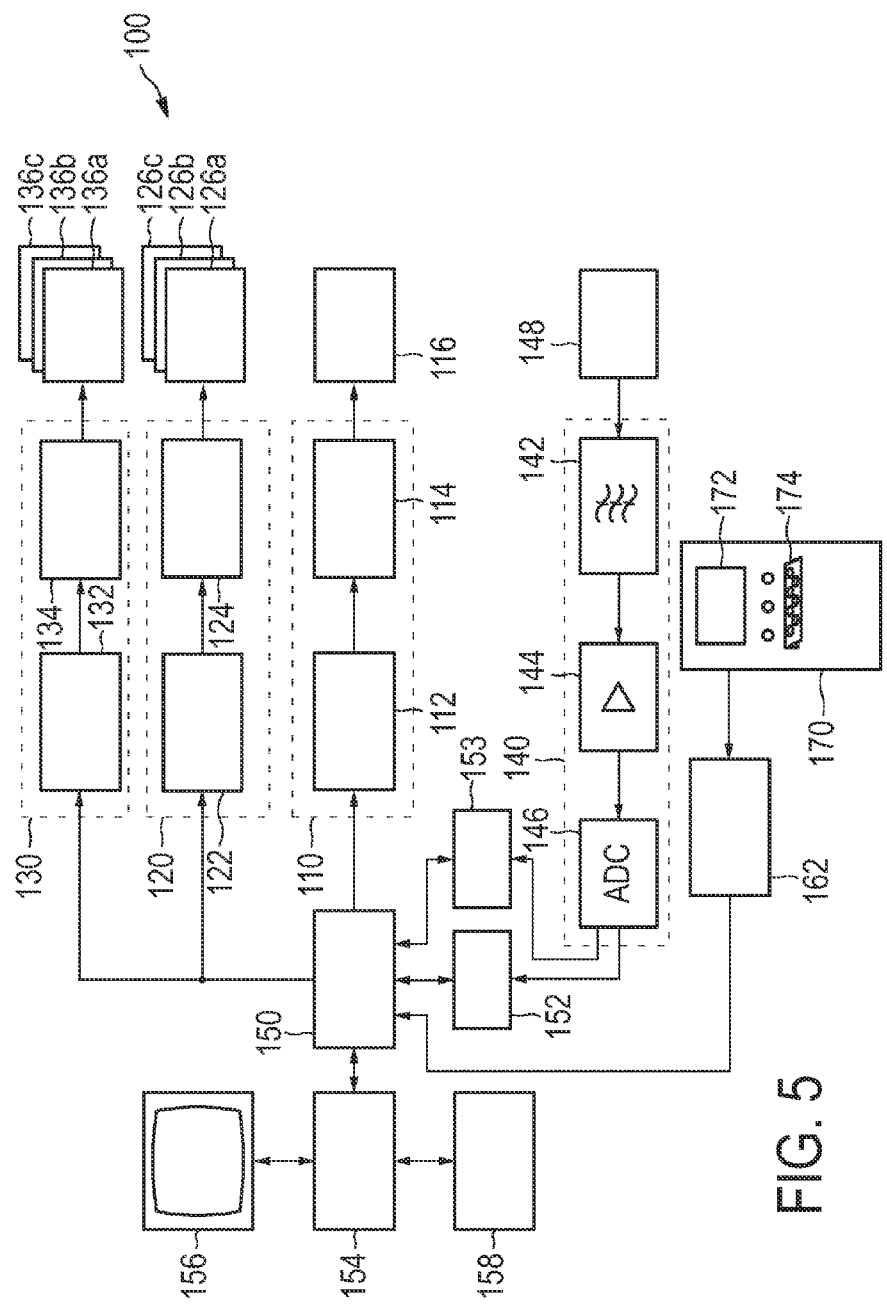
FIG. 5 shows a block diagram of a second embodiment of the MPI apparatus according to the present invention.

FIGS. 4 and 5 show a general block diagram of an MPI apparatus 10 according to a first and second embodiment of the present invention. The general principles of magnetic particle imaging explained above are valid and applicable to this embodiment as well, unless otherwise specified. For example, the selection, focus and processing means, which are not obligatory for the apparatus according to the present invention, are not included in the first embodiment according to the present invention (see FIG. 4). The apparatus according to the first embodiment of the present invention thus does neither make use of means to actively move the magnetic pressure measurement device 60, 70 (see FIGS. 6 and 7) nor does it make use of the MPI imaging technique. In contrast thereto, the second embodiment of the present invention (shown in FIG. 5) includes all above-mentioned means, the selection means, the focus means and the processing means.

The major elements of the first embodiment of the apparatus shown in FIG. 4 are magnetic field generating means 130, 136, receiving means 140, 148 and evaluation means 153. The functions of these means shall be explained in an MPI mode in the following.

For generating a magnetic field for influencing the magnetization of the magnetic pressure measurement device 60, 70 the apparatus 100 comprises magnetic field generating means which itself comprise a subset of magnetic field coils, preferably three pairs 136a, 136b, 136c of oppositely arranged magnetic coil elements. These magnetic field coils 136a, 136b, 136c are controlled by a magnetic field signal generator unit 130, preferably comprising a separate magnetic field signal generation subunit for each coil element (or at least each pair of coil elements) of said set of magnetic field coils 136a, 136b, 136c. Said magnetic field signal generator unit 130 comprises a magnetic field current source 132 (preferably including a current amplifier) and filter unit 134 for providing a magnetic field current to the respective magnetic field coils 136a, 136b, 136c. The magnetic field current source 132 is adapted for generating an AC current and is also controlled by a control unit 150.

The above-described magnetic field generating means are, as already mentioned, adapted for generating a magnetic field in order to influence the magnetization of the magnetic pressure measurement device 60, 70. In order to acquire detection signals which are caused by the induced changes of the magnetization of the magnetic pressure measurement device 60, 70 receiving means 148 are furthermore provided according to the first embodiment of the present invention. These detection signals furthermore depend on the changes of the physical properties of the magnetic pressure measurement device 60, 70 which are caused by the internal pressure of the examination object.

According to the present invention these changes of the physical properties basically mean a change of the shape of the magnetic pressure measurement device 60, 70 which occur due to the induced pressure within the examination object. In other words this means that, due to the deformable characteristics of the magnetic pressure measurement device 60, 70, the magnetization curve (the B-H curve) of the magnetic pressure measurement device 60, 70 is changed due to the pressure which has an influence on the acquired detection signals. In particular, the demagnetization factor is reduced if the device 60, 70 is compressed and therefore elongated so that thereby the steepness of the B-H curve is increased.

In the following, the special arrangement of the receiving means 148 and the signal detection according to the present invention shall be explained in detail.

The signal detection is besides the receiving means 148 additionally supported by a signal receiving unit 140, which receives signals detected by said receiving means 148. Said signal receiving unit 140 comprises a filter unit 142 for filtering the received detection signals. The aim of this filtering is to separate measured values from other, interfering signals. To this end, the filter unit 142 may be designed for example such that signals which have temporal frequencies that are smaller than the temporal frequencies with which the receiving means 148 are operated, or which are above these temporal frequencies, do not pass the filter unit 142. These signals are then transmitted via an amplifier unit 144 to an analog/digital converter 146 (ADC). The digitalized signals produced by the ADC 146 are finally lead to an evaluation means 153, which evaluates the detection signals in order to determine the internal pressure of the examination object.

These evaluation means 153 evaluate the changes of the magnetic anisotropy of the magnetic pressure measurement device 60, 70 which are caused by the pressure-induced shape changes of the device 60, 70. The internal pressure of the examination object can thereby be determined for example using a mechanical modeling of the magnetic pressure measurement device 60, 70. In practice, the acquired detection signals are furthermore compared with known reference signals which improves the quality of the determination of the internal pressure measurement. In order to acquire such reference signals the B-H curve of the device 60, 70 is measured for different temperatures and pressures when a magnetic field as the one mentioned above is applied. In this way, the magnetic pressure measurement device 60, 70 can be reliably calibrated.

Furthermore, as can be seen from FIG. 4 a control unit 150 is provided according to the first embodiment of the present invention which is adapted for controlling the signal generator unit 130 to generate and provide control currents to the respective field coils to generate the above-mentioned magnetic field for influencing the magnetization of the magnetic pressure measurement device 60, 70. Since the characteristics of the magnetic field, especially the frequency of the applied magnetic field, needs to be known for the evaluation respectively the determination of the pressure, the control unit 150 is also connected to the evaluation means 153.

FIG. 5 shows a block diagram of second embodiment of the MPI apparatus according to the present invention. This apparatus 100 is, compared to the first embodiment, further extended and includes various additional MPI means as the ones shown in the exemplary embodiments of FIGS. 1 and 3. For example, magnetic selection means, focus means and processing means 154 are additionally provided. The apparatus 100 according to the second embodiment of the present invention is therefore also able to use more than one magnetic pressure measurement device 60, 70 within one measurement, and the device 60, 70 can be actively moved, tracked and imaged which represents a further significant improvement compared to the first embodiment.

For generating the magnetic gradient selection field explained above, selection means are provided comprising a set of selection field (SF) coils 116, preferably comprising at least one pair of coil elements. The selection means further comprises a selection field signal generator unit 110. Preferably, a separate generator subunit is provided for each coil element (or each pair of coil elements) of said set 116 of selection field coils. Said selection field signal generator unit 110 comprises a controllable selection field current source 112 (generally including an amplifier) and a filter unit 114 which provide the respective section of the field coil element with the selection field current to individually set the gradient strength of the selection field in the desired direction. Preferably, a DC current is provided. If the selection field coil elements 116 are arranged as opposed coils, e.g. on opposite sides of the field of view 28, the selection field currents of opposed coils are preferably oppositely oriented. The selection field signal generator unit 110 is controlled by the control unit 150 such that the sum of the field strength and the sum of the gradient strength of all spatial fractions of the selection field is maintained at a predefined level.

The selection field is especially advantageous since it can be used for focusing on one desired magnetic pressure measurement device 60, 70 if a greater number of devices is used. In this case only devices 60, 70 located at the FFP of the selection field contribute to the detection signals since all other devices 60, 70 which are located outside the FFP are kept in the state of saturation. Furthermore, influences of other magnetic contaminations can be suppressed using the selection field. A still further major advantage of the magnetic selection field is that it can be used as a barrier for the magnetic pressure measurement device 60, 70 so that the device 60, 70 cannot pass a certain position. For example, if the pressure is measured in a vessel the FFP can be placed on one end of the examination area within the vessel. Then the device 60, 70 is always driven towards this point by the blood flow but due to the gradient characteristics of the magnetic selection field the device 60, 70 is always pulled back from the FFP against the blood flow so that the device 60, 70 does not leave the examination area and is not transported further away with the blood flow.

As already mentioned above, the apparatus 100 according to the second embodiment of the present invention further comprises focus means. These focus means comprise a set of focus field (FF) coils, preferably three pairs 126a, 126b, 126c of oppositely arranged focus field coil elements. Set magnetic focus field is generally used for changing the position in space of the field of view 28. The focus field coils are controlled by a focus field signal generator unit 120, preferably comprising a separate focus field signal generation subunit for each coil element (or at least each pair of coil elements) of said set of focus field coils. Said focus field signal generator unit 120 comprises a focus field current source 122 (preferably comprising a current amplifier) and a filter unit 124 for providing a focus field current to the respective coil of said subset of coils 126a, 126b, 126c which shall be used for generating the magnetic focus field. The focus field signal generator unit 120 is also controlled by the control unit 150.

In summary this means that by additionally using focus means the position in space of the field of view 28 can be changed magnetically, whereas according to the first embodiment (without focus means), the examination object (e.g. the patient) needs to be moved manually in order to change the position in space of the field of view 28 with respect to the examination object. This is especially necessary since the field of view 28 has a very limited size so that, if the magnetic pressure measurement device 60, 70 needs to be moved over a longer distance within the examination object, the focus field needs to change the position in space of the field of view 28 in order to actively move and track the device 60, 70 over its entire path until it has reached its desired position. In other words, the focus field replaces the active mechanical movement of the examination object, this means that in case of a human patient, the patient would need to be moved physically in order to move the field of view if no focus field means are provided.

Furthermore, the magnetic focus field coils 126a, 126b, 126c can be used to actively move the device 60, 70 through the examination object, e.g. to actively move the device 60, 70 through the arteries until its final position within the pulmonary arteries where the pressure shall be measured. The coils 126a, 126b, 126c are able to generate sufficiently homogenous fields in various directions at a sufficiently high speed and with sufficiently large field strengths that are required for the movement of the magnetic pressure measurement device 60, 70. Theoretically, also the selection or the drive means could be used for this active movement of the device 60, 70.

For moving the magnetic pressure measurement device 60, 70 through the examination object (e.g. through the arteries) in a direction instructed by movement commands, the control unit 150 is adapted for controlling the signal generator units 110, 120, 130 to generate and provide control currents to the respective field coils to generate appropriate magnetic fields. It is thereby not only possible to actively move the device 60, 70, the device 60, 70 can also be kept respectively hold at a constant position, in particular by use of a feedback mechanism based on real-time positioning.

According to the second embodiment of the present invention the receiving means 148 are furthermore adapted to acquire detection signals which can then be processed in order to reconstruct an image of the position and the surroundings of the device 60, 70. The digitalized signals are therefore lead to an image processing unit (also called reconstruction means) 152, which reconstructs the spatial distribution of the magnetic material of the magnetic pressure measurement device 60, 70 from these signals. The reconstructed spatial distribution is finally transmitted via the control unit 150 to a computer 154 which displays the image on a monitor 156. Thus, an image can be displayed showing the position of the device 60, 70 within the examination object.

For the active input of the above-mentioned movement commands, an interface 162 is furthermore provided according to the second embodiment of the present invention. Said interface 162 can be implemented in various ways. For instance, said interface 162 can be a user interface by which the user manually input user commands, such as via a keyboard, a console, a joystick or a navigation tool, e.g. installed on a separate computer (not shown). In another implementation said interface 162 is an interface for a connection to an external device for movement control, such as a navigation unit, by use of which the movement of the device 60, 70 has been planned an advance, e.g. based on image data of the examination object acquired in advance by another imaging modality, such as MR (magnetic resonance) or CT (computer tomography). The interface 162 then receives information about the desired movement and the desired position for placing the device 60, 70 within the examination object, and the interface 162 of the control unit 150 is able to "translate" said commands into movement commands for the respective signal generator units 110, 120, 130.

Via the interface 162 movement commands are received from an external movement control unit 170 comprising a display 172, e.g. for displaying free-acquired image data of the examination object, and an operator control 174 for inserting control commands for planning the movement of the magnetic pressure measurement device 60, 70.

In a practical intervention, the surgeon will plan the intervention using the movement control unit 170. The navigation plan, which particular includes the movement control commands and the desired position to place the magnetic pressure measurement device 60, 70 is then provided via the interface to the control unit 150 of the MPI apparatus 100. The control unit 150 then controls the movement of the device 60, 70 within the examination object.

Hence, in effect, the apparatus according to the second embodiment of the present invention is able to actively move the device 60, 70 through the examination object, in particular to control the direction of movement of the device 60, 70 based on movement commands, and to control the placement of the magnetic pressure measurement device 60, 70 at the desired position within the examination object irrespective in which form and by whom or what the movement commands have been provided. When the device 60, 70 has reached its final position within the examination object, the internal pressure of the examination object can then be measured using the above-mentioned pressure measurement technique.

Figure 6:
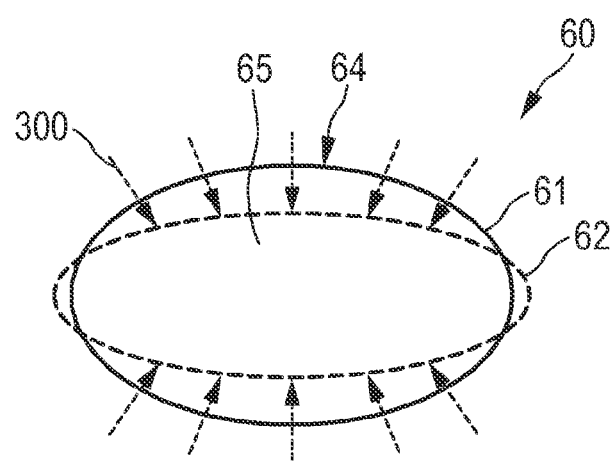
FIG. 6 shows a first embodiment of a magnetic pressure measurement device according to the present invention.
Figure 7:
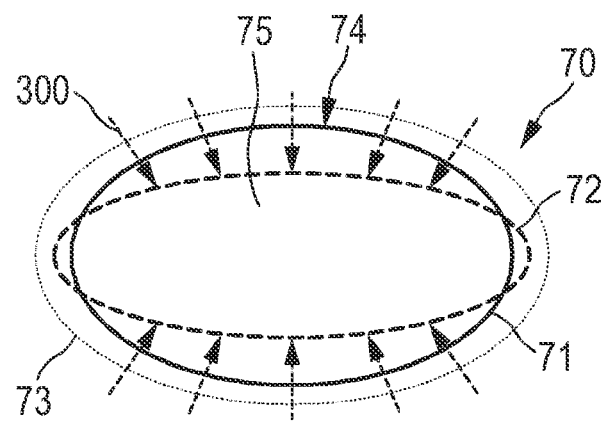
FIG. 7 shows a second embodiment of the magnetic pressure measurement device according to the present invention.

FIGS. 6 and 7 show a first and second embodiment of the magnetic pressure measurement device 60, 70 according to the present invention. In these figures the internal pressure of the examination object is indicated by dashed arrows. For simplicity reasons a hydrostatic pressure is assumed. Of course, also other non-hydrostatic pressure states can be measured with the magnetic pressure measurement device 60, 70 according to the present invention.

As already mentioned above, the magnetic pressure measurement device 60, 70 is preferably made of a pure iron mantel 64, 74 which is filled with gas 65, 75. The magnetic pressure measurement device 60, 70 is therefore deformable. During the measurement the magnetic pressure measurement device 60, 70 changes its shape due to the induced pressure 300 in the examination object. If the pressure 300 is increased, the magnetic pressure measurement device 60, 70 is compressed like a balloon from an expanded state 61, 71 to a compressed state 62, 72. As already explained above, the B-H curve of the magnetic pressure measurement device 60, 70 changes, respectively gets steeper, when the pressure 300 is increased and the device 60, 70 is compressed (62, 72).

Furthermore, it is preferred that the magnetic pressure measurement device 60, 70 has an elongated shape, in particular an ellipsoidal shape in order to have a considerably high magnetic anisotropy. It has to be noted that of course other shapes (e.g. a spherical shape) than the one indicated are possible. By example, the length for the magnetic pressure measurement device 60, 70 is preferably in the range of about 50 µm.

In comparison to the first embodiment of the magnetic pressure measurement device 60, the magnetic pressure measurement device 70 according to the second embodiment (shown in FIG. 7) is additionally provided with a protective casing 73. This protective casing 73 allows the device 70 to still freely change its shape, i.e. to change its shape from the expanded state 71 to the compressed state 72 and vice versa, even when the magnetic pressure measurement device 70 gets stuck. This usually happens during a measurement when the device 70 enters the very thin lung capillaries where it gets stuck. If not equipped with such a protective casing 73, the magnetic pressure measurement device 70 would then lose its function since a freely (only pressure-induced) shape change would not be possible anymore. This would, of course, lead to misunderstanding and wrong detection signals.

The above-mentioned situation where the device 60, 70 gets stuck for example in a lung artery, is schematically shown by example in FIGS. 8-10. FIGS. 8, 9, 10 thereby exemplify the different possibilities how to overcome the situation where the device is stuck in order to still being able to receive reliable and correct detection signals.

In FIG. 8A the magnetic pressure measurement device 60 (not equipped with a protective casing) is schematically shown in the situation where it is stuck in the tissue 310. A magnetic gradient field 320, which is for simplicity reasons indicated by simplified straight field lines showing the direction of the strongest gradient, can be applied in order to pull respectively drag out the device 60 of its stuck position. In this way, the device 60 is moved away from the tissue 310 (the movement direction is indicated by an arrow). As soon as the device 60 is far enough away from the tissue 310 so that it can freely be expanded and compressed by the induced pressure, the applied homogeneous magnetic field 320 can be turned off so that the device 60 flows back to its original position due to the blood flow. While freely flowing through the artery respectively the capillary, the drive and the detection field (in FIG. 8C indicated for simplicity reasons by sinusoidal lines 330) is turned on in order to acquire the desired detection signals by use of which the internal pressure of the artery respectively the capillary can be measured.

FIG. 9A-9C show the same situation (the magnetic pressure measurement device 60 is also not equipped with a protective casing) and the same technique for dragging out the device 60 of the tissue 310. The only difference is that the magnetic gradient field 320 is constantly turned on in a way that the device 60 is kept at a constant position (indicated by two oppositely oriented arrows) so that the detection signals can be acquired over a longer time by superposing the above-mentioned frequency field (drive field) indicated by the sinusoidal lines 330 shown in FIG. 9C.

Figure 10A:
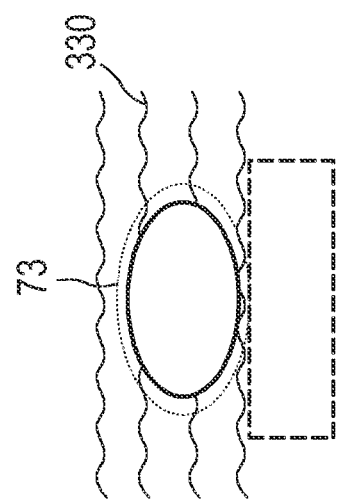
FIGS. 10A and 10B show a third embodiment of the measurement procedure in a schematic and simplified manner.
Figure 10B:
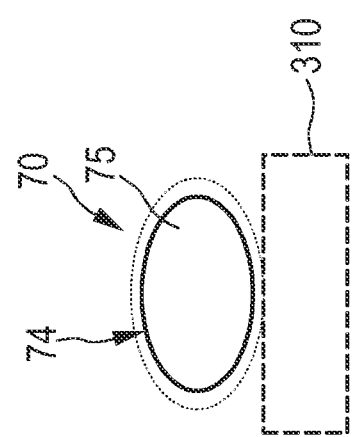

FIGS. 10A and 10B show the third possibility to overcome the given situation. Here, the magnetic pressure measurement device 70 is equipped with a protective casing 73 so that, as already mentioned above with respect to FIG. 7, correct detection signals can even be acquired when the device 70 is stuck in the tissue 310.

Figure 11A:
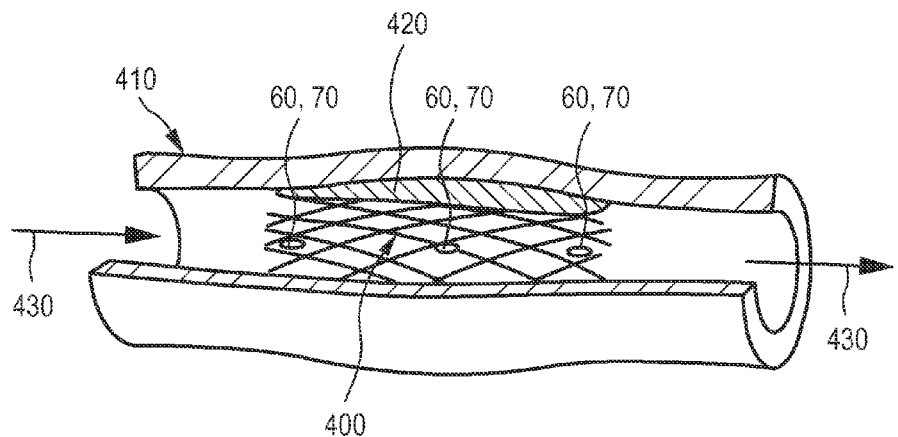
FIGS. 11A and 11B show the magnetic pressure measurement device according to the present invention attached to a stent, which is inserted into an artery, in a schematic side view and a cross-sectional view.
Figure 11B:
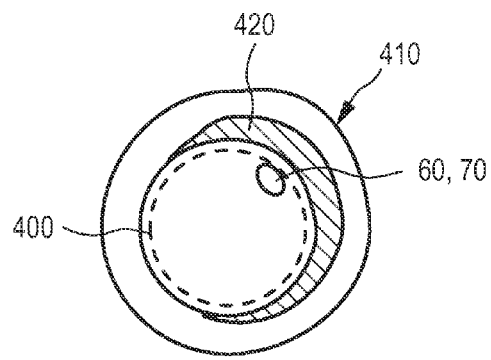

FIGS. 11A and 11B show an embodiment in which the magnetic pressure measurement device 60, 70 according to the present invention is attached to a stent 400 which is inserted into an artery 410. Especially in case of the occurrence of plaque 420 within an artery 410 or a restenosis it is desirable to measure the pressure within an artery 410 in order to monitor the blood flow (indicated with arrows 430) at this part of the artery 410 and to identify unwanted changes, which, for example, occur due to increased plaque. As exemplarily shown in FIG. 11 several magnetic pressure measurement devices 60, 70 are attached to the stent 400, e.g. at each side and in the middle part of the stent 400. This enables measuring the pressure in front of, in, behind, as well as outside of the stent in the above described way making use of the MPI technique. It is to be understood that, depending on the application, the number of magnetic pressure measurement devices 60, 70 can, of course, vary, i.e. being much higher or also just one or two. The magnetic pressure measurement device 60,70 can also be attached to stent grafts and integrated into Gugliemi detachable coils. Thereby, it is preferable that the stents, stent grafts or Gugliemi detachable coils respectively are made of non-ferromagnetic metal in order to separate the responses of the magnetic pressure measurement device 60,70 and the fixation device 400 (stent, stent graft or Gugliemi detachable coil). It is further preferable to make the stent, stent graft or Gugliemi detachable coil from non- or low-conductive material in order to avoid possible device heating due to the induced electrical currents.

In summary, an apparatus and a method is presented which enables to non-invasively measure the internal pressure of an examination object, in particular the internal pressure of the pulmonary artery without a surgical intervention using the MPI technique. In the case of pulmonary artery pressure measurement a very small magnetic pressure measurement device is steered through the artery using appropriate magnetic fields. Thereby it can be tracked, and even imaged using the MPI imaging technique. Due to a special evaluation process the pressure-induced shape change of the magnetic pressure measurement device can be evaluated in order to determine the pressure within the pulmonary artery. In contrast to the known pulmonary artery catheterization this method presents a significant effort for the modern medicine since no surgical intervention is longer necessary, and therefore the examination is much more comfortable and absolutely riskless for the patient. Additionally the time for conducting the examination is significantly reduced and the pressure can be measured at any desired place within the pulmonary artery.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measured cannot be used to advantage.

Any reference signs in the claims should not be construed as limiting the scope.

The invention claimed is:

1. An apparatus for measuring an internal pressure of an examination object by use of a magnetic pressure measurement device having a ferromagnetic body introduced into the examination object, which apparatus comprises:
    a magnetic field generator comprising magnetic field signal generator units and magnetic field coils said magnetic field generator is configured to generate a magnetic field for changing a magnetization of the magnetic pressure measurement device,
    a receiver comprising at least one signal receiving unit and at least one receiving coil, said receiver is configured to acquire detection signals, which detection signals depend on changes in magnetization of the ferromagnetic body of the magnetic pressure measurement device caused by the magnetic field and on changes of physical properties of the magnetic pressure measurement device caused by the internal pressure of the examination object, and
    an evaluation device that is configured to evaluate the detection signals of the magnetic pressure measurement device for determining the internal pressure of the examination object.

2. An apparatus as claimed in claim 1, wherein the receiver is adapted to acquire detection signals which depend on changes of a shape of the magnetic pressure measurement device.

3. An apparatus as claimed in claim 1, wherein the evaluation device is adapted to evaluate a change of magnetic anisotropy of the magnetic pressure measurement device caused by a change of a shape of the magnetic pressure measurement device.

4. An apparatus as claimed in claim 1, wherein the evaluation device is adapted to evaluate a change of mechanical resonance of the magnetic pressure measurement device caused by a change of a shape of the magnetic pressure measurement device.

5. An apparatus as claimed in claim 1, wherein the evaluation device is adapted to determine the internal pressure of the examination object by comparing acquired detection signals with known reference signals.

6. An apparatus as claimed in claim 1, further comprising a selection device comprising a selection field signal generator unit and selection field elements, said selection device is adapted to generate a magnetic selection field in a field of view having a pattern in space of its magnetic field strength such that a first sub-zone has a low magnetic field strength wherein the magnetization of the magnetic pressure measurement device is not saturated and a second sub-zone has a higher magnetic field strength wherein the magnetization of the magnetic pressure measurement device is saturated.

7. An apparatus as claimed in claim 6, wherein the magnetic field generator is adapted to change a position in space of the first and second sub-zones in the field of view by means of a magnetic drive field so that the magnetization of the magnetic pressure measurement device changes locally.

8. An apparatus as claimed in claim 7, further comprising a focusing device comprising a focus field signal generator unit and focus field coils said focusing device is adapted to change the position in space of the field of view by means of a magnetic focus field.

9. An apparatus as claimed in claim 1, further comprising a control device which is adapted to control said signal generator units in order to generate and provide control currents to respective field coils to generate appropriate magnetic fields for moving the magnetic pressure measurement device through the examination object in a direction instructed by movement commands and for holding the magnetic pressure measurement device at a constant position by use of a feedback mechanism based on real-time positioning.

10. An apparatus as claimed in claim 1, further comprising processing means for processing the detection signals acquired when appropriate magnetic fields are applied for localizing the magnetic pressure measurement device within the examination object and for determining a position in space of the magnetic pressure measurement device within the examination object from processed detection signals.

11. An apparatus as claimed in claim 1, wherein the magnetic pressure measurement device is attached to or integrated within a fixation device comprising a stent, a stent graft or a Guglielmi detachable coil, wherein the fixation device is placed at a fixed position within the examination object.

12. A magnetic pressure measurement device for the use in an apparatus as claimed in claim 1, wherein said magnetic pressure measurement device is a deformable ferromagnetic magnetically anisotropic, body comprising a hollow, at least partially ellipsoidal or spherical-like body.

13. A magnetic pressure measurement device as claimed in claim 12, which further comprises a protective casing so that the magnetic pressure measurement device is free to change its shape within this protective casing.

14. A non-transitory computer-readable medium storing a program, which, when executed by at least one processor, causes the at least one processor to control an apparatus as claimed in claim 1.

15. A method for measuring an internal pressure of an examination object by use of a magnetic pressure measurement device introduced into the examination object, which method comprises the steps of:
    generating a magnetic field for changing a magnetization of the magnetic pressure measurement device,
    acquiring detection signals, which detection signals depend on changes in the magnetization of the magnetic pressure measurement device caused by the magnetic field and on changes of physical properties of the magnetic pressure measurement device caused by the internal pressure of the examination object, and
    evaluating the detection signals of the magnetic pressure measurement device for determining the internal pressure of the examination object.

* * * * *